US009016399B2

(12) United States Patent
Pelletier et al.

(10) Patent No.: US 9,016,399 B2
(45) Date of Patent: Apr. 28, 2015

(54) APPARATUS AND METHODS FOR LITHOLOGY AND MINERALOGY DETERMINATIONS

(75) Inventors: Michael T. Pelletier, Houston, TX (US); Christopher Michael Jones, Houston, TX (US); Paul F. Rodney, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/004,448

(22) PCT Filed: Mar. 23, 2011

(86) PCT No.: PCT/US2011/029666
§ 371 (c)(1),
(2), (4) Date: Sep. 11, 2013

(87) PCT Pub. No.: WO2012/128764
PCT Pub. Date: Sep. 27, 2012

(65) Prior Publication Data
US 2014/0020954 A1 Jan. 23, 2014

(51) Int. Cl.
*E21B 49/00* (2006.01)
*G01J 3/28* (2006.01)
(Continued)

(52) U.S. Cl.
CPC .............. *E21B 49/005* (2013.01); *G01J 3/2823* (2013.01); *G01N 21/3563* (2013.01); *G01V 99/00* (2013.01); *G01N 21/31* (2013.01); *G01N 2021/3155* (2013.01); *G01N 33/18* (2013.01); *G01N 33/1826* (2013.01); *G01V 8/10* (2013.01)

(58) Field of Classification Search
CPC ...... E21B 49/005; E21B 49/00; E21B 47/101; E21B 49/08; E21B 49/10; E21B 2049/085; G01J 3/2823; G01N 21/3563; G01N 99/00; G01N 21/31; G01N 33/1826; G01N 2021/3155; G01N 33/18
USPC ................... 175/50, 58; 166/250.01, 264, 66; 73/152.18, 152.23; 348/81, 135; 348/E7.085; 356/402
See application file for complete search history.

(56) References Cited

U.S. PATENT DOCUMENTS 5,528,295 A 6/1996 Wagner
8,081,802 B2 * 12/2011 Dvorkin et al. ............... 382/109
(Continued)

FOREIGN PATENT DOCUMENTS

EP 1862795 A1 12/2007
GB 2225110 A 5/1990
WO 02/061239 A1 8/2002

OTHER PUBLICATIONS

Zhan, Yunjun et al., "Hyperspectral Remote Sensing Rock and Mineral Spectral Feature Mining Based on Rough Set Theory," Computer Science and Software Engineering, 2008 International Conference on; IEEE, Piscataway, New Jersey, Dec. 12, 2008, pp. 470-473.
(Continued)

*Primary Examiner* — Young-Suk (Philip) Ro
(74) *Attorney, Agent, or Firm* — Benjamin Fite; Baker Botts L.L.P.

(57) ABSTRACT

A well bore is drilled in the formation. Cuttings are retrieved from the well bore while drilling the formation and a hyperspectral image of the cuttings is continuously obtained. The hyperspectral image of the cuttings is analyzed to determine formation characteristics.

22 Claims, 15 Drawing Sheets

(51) Int. Cl.
*G01N 21/3563* (2014.01)
*G01V 99/00* (2009.01)
*G01N 21/31* (2006.01)
*G01N 33/18* (2006.01)
*G01V 8/10* (2006.01)

(56) References Cited

U.S. PATENT DOCUMENTS

2009/0309960 A1  12/2009  Park et al.
2011/0042143 A1*  2/2011  Auranen et al. .......... 175/58

OTHER PUBLICATIONS

International Preliminary Report on Patentability for PCT Application No. PCT/US2011/029666, dated Nov. 20, 2013, 14 pages.
International Search Report and Written Opinion, International Application No. PCT/US2011/029666, 13 pgs., Feb. 2, 2012.
Yunjun, Zhan et al., "Hyperspectral Remote Sensing Rock and Mineral Spectral Feature Mining Based on Rough Set Theory," Computer Science and Software Engineering, 2008 International Conference on; IEEE, Piscataway, New Jersey, Dec. 12, 2008, pp. 470-473.
Office Action issued in related European Patent Application No. 11712416.4 mailed Sep. 22, 2014, 6 pages.

* cited by examiner

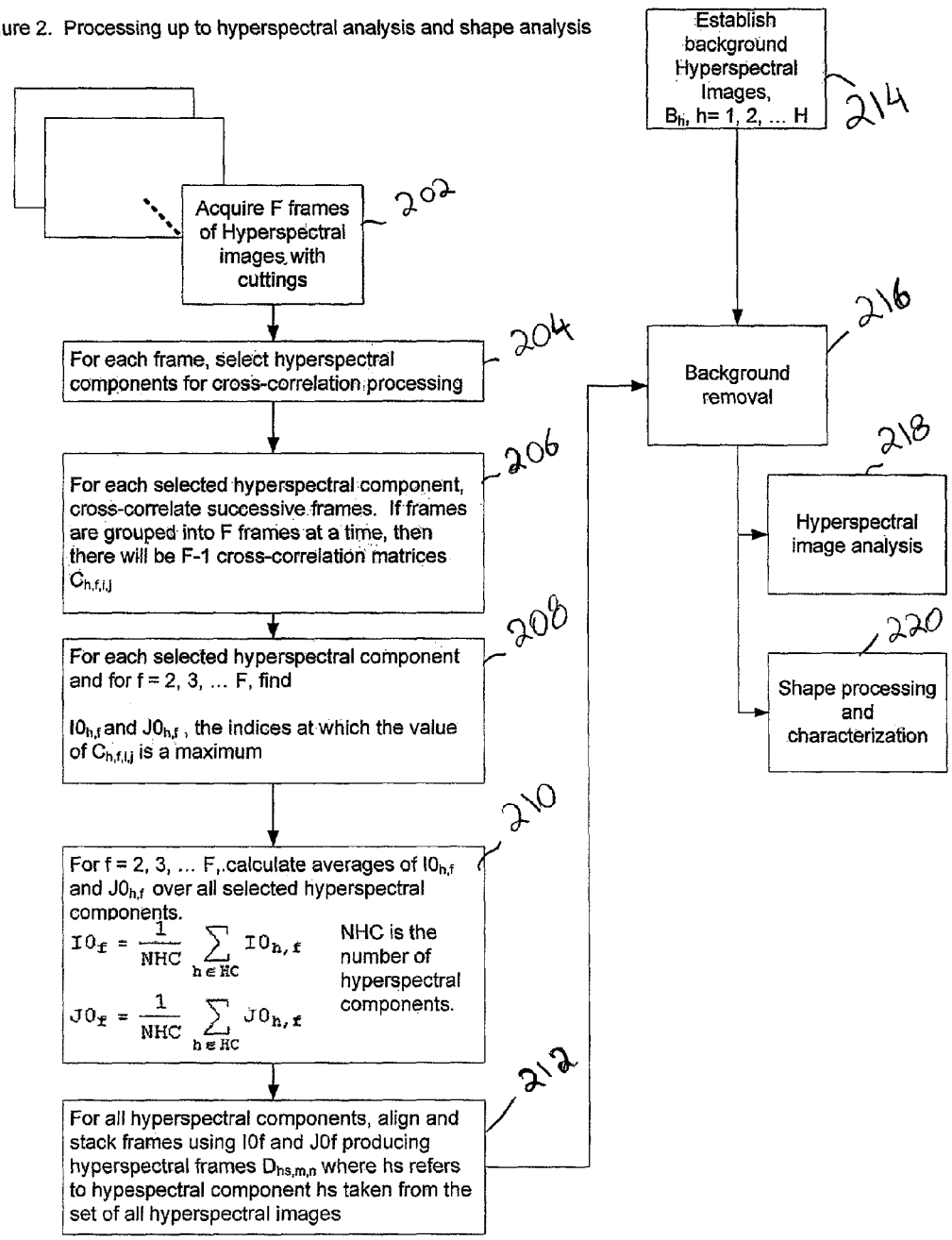

APPARATUS AND METHODS FOR LITHOLOGY AND MINERALOGY DETERMINATIONS

RELATED APPLICATION

This application is a U.S. National Stage Application of International Application No. PCT/US2011/029666 filed Mar. 23, 2011, and is hereby incorporated by reference in its entirety.

BACKGROUND

When performing operations directed to obtaining hydrocarbons from a subterranean formation it is often desirable to perform an analysis of the subterranean formation. The characteristics of the subterranean formation may be used to ensure efficient and successful operations. One way to characterize the subterranean formation in which the hydrocarbon operations are being performed is to analyze the formation during the drilling operations.

Drilling fluids (also referred to herein as "drilling muds") are often circulated downhole during drilling operations in a subterranean formation. The drilling fluids perform a number of functions, including lubricating the area being drilled and removing any cuttings that are created during the drilling operations. When the drilling fluids are returned to the surface, they may be directed to a shale shaker. The returned drilling fluids typically includes a mixture of the drilling fluid that was pumped downhole and cutting from the region that is being drilled. This mixture may be directed to a shale shaker. The fluid portion of the mixture may pass through screens in the shale shaker while the cuttings remain on the screen.

Once the fluid portion of the returned mixture is separated from the cuttings, a mud logger may periodically go to the shale shaker and select certain cuttings which he deems are representative of the cuttings that are returned to the surface with the drilling fluid during a particular time period. The selected samples of the cuttings are removed from the screen and the mud logger may then prepare them for further analysis by, for example, washing them. The mud logger may then select one or two of the previously selected cutting samples to analyze as a way to determine the mineralogy of the formation being drilled. This small group of samples may then be smashed into a powder which can be analyzed using LASER spectroscopy or other methods to determine the elemental composition of the samples in order to infer the formation mineralogy.

The current methods of analyzing the mineralogy of the formation based on the cuttings that are returned to the surface with the drilling fluids has several disadvantages. First, the current methods do not provide a continuous analysis of the cuttings that are returned to the surface due to the time lag between the time the different samples are taken by the mud logger. Moreover, the current methods are inherently subject to human error and inaccuracies since the mud logger selects the samples that he deems are representative of the cuttings being returned to the surface during a given time period. Further, the current methods are labor intensive as they require personnel to manually select and process sample cuttings and analyze them to determine the formation mineralogy. Additionally, because a limited number of samples are taken at a given time, the operator cannot obtain a wide area view of the mineralogy and/or lithology of the cuttings.

BRIEF DESCRIPTION OF THE DRAWINGS

FIG. 2 shows a process for hyperspectral analysis and shape analysis of images in accordance with an exemplary embodiment of the present invention;

FIG. 4 is a contour plot of the pebble bed of FIG. 3a.

FIG. 8 shows the relationship between the calculated area and the step size for the image of FIG. 3a.

FIG. 14 shows a two-dimensional Fourier transform of the image of FIG. 3a.

While embodiments of this disclosure have been depicted and described and are defined by reference to example embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The terms "couple" or "couples," as used herein are intended to mean either an indirect or direct connection. Thus, if a first device couples to a second device, that connection may be through a direct connection, or through an indirect electrical connection via other devices and connections. The term "upstream" as used herein means along a flow path towards the source of the flow, and the term "downstream" as used herein means along a flow path away from the source of the flow. The term "uphole" as used herein means along the drillstring or the hole from the distal end towards the surface, and "downhole" as used herein means along the drillstring or the hole from the surface towards the distal end.

It will be understood that the term "oil well drilling equipment" or "oil well drilling system" is not intended to limit the use of the equipment and processes described with those terms to drilling an oil well. The terms also encompass drilling natural gas wells or hydrocarbon wells in general. Further, such wells can be used for production, monitoring, or injection in relation to the recovery of hydrocarbons or other materials from the subsurface. In addition, the teachings of this invention can be used to monitor the cuttings from mining operations, such as coal mining, mining for minerals, etc.

Figure 1:
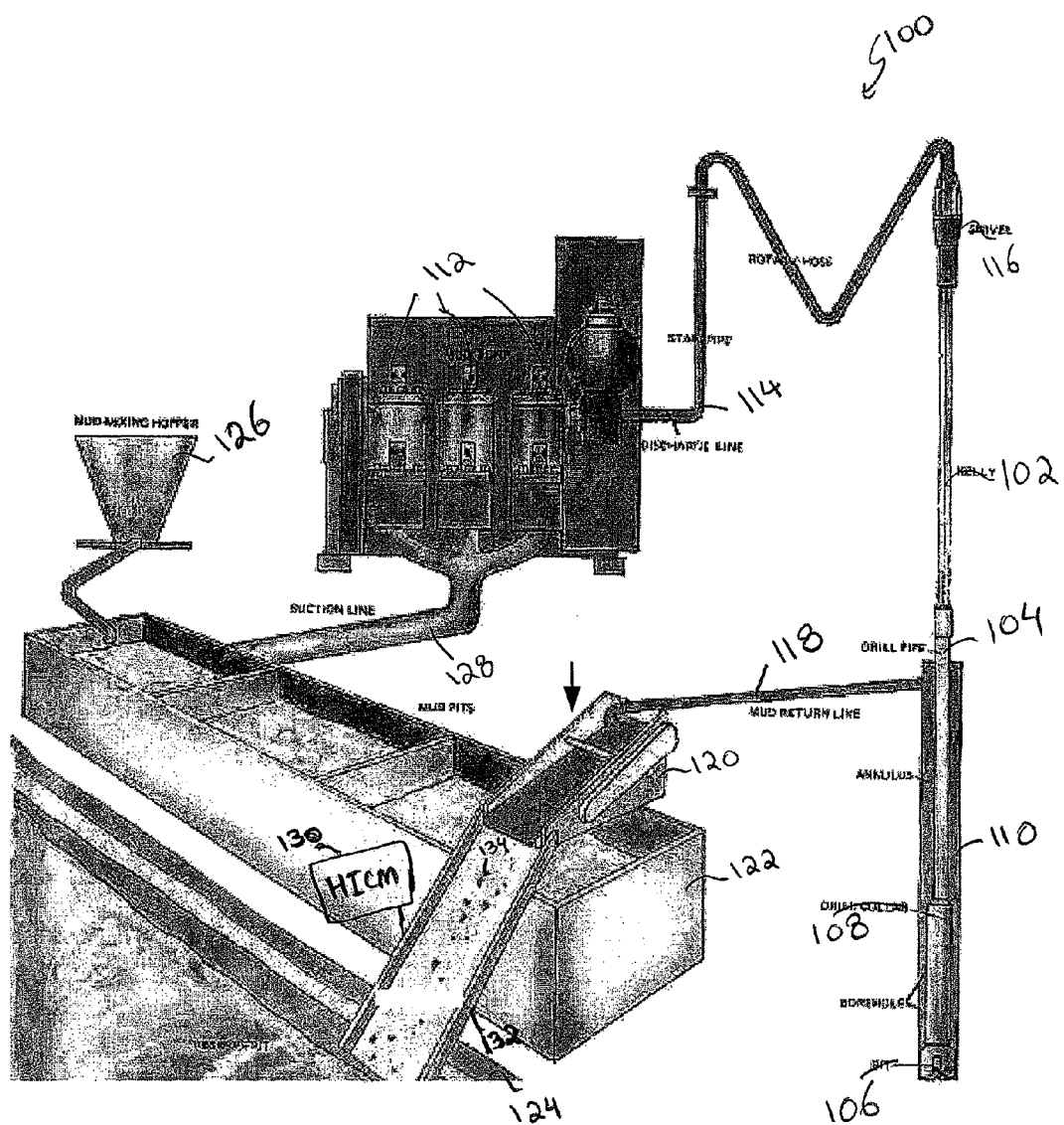
FIG. 1 shows an illustrative drilling rig in accordance with an exemplary embodiment of the present invention.

Turning now to FIG. 1, an illustrative drilling rig in accordance with an exemplary embodiment of the present invention is depicted generally with reference numeral 100. In one exemplary embodiment, a Kelly 102 may support one more drilling pipes 104 which are coupled to a drill bit 106 through a drill collar 108. As the drill bit 106 penetrates the subterranean formation and forms the wellbore 110 the drilling pipes 104 remain coupled to the drilling bit 106 to deliver drilling fluids to the region being drilled. One or more discharge pumps 112 may pump the drilling fluid to the drilling pipes 104 through a discharge line 114 which is coupled to the drill pipes 104 through a swivel 116 and the Kelly 102.

As would be appreciated by those of ordinary skill in the art, with the benefit of this disclosure, the drilling fluids may be directed downhole through the drilling pipes 104 and return to the surface through the annulus between the drilling pipes 104 and the wellbore 110 or they may be directed downhole through the annulus between the drilling pipes 104 and the wellbore 110 and returned to the surface through the drilling pipe 104 in accordance with embodiments of the present application.

Once the mixture of the drilling fluid and the cuttings from the formation that result from the drilling operations are returned to the surface they are directed to a mud return line 118 which directs the returned mixture to the shale shaker 120. The shale shaker 120 may include a vibrating mesh that separates the cuttings from the returned drilling fluid. Once at the shale shaker 120, the fluid portion of the returned mixture which consists of the drilling fluid seeps through screens and into mud pits 122 and the cuttings that remain on the screens (i.e. are larger than the shale shaker 120 screen mesh size) are directed to a cutting disposal area 124. In one embodiment, a mud mixing hopper 126 may be used to add materials to the returned drilling fluid that is directed to the mud pits 122. If no materials are added, the returned drilling fluid simply passes through the mud pits 122. A suction line 128 directs the returned drilling fluids from the mud pits 122 to the discharge pumps 112. The discharge pumps may then recirculate the drilling fluid downhole to the portion of the subterranean formation that is being drilled.

In accordance with an exemplary embodiment of the present invention, a hyperspectral image capture mechanism ("HICM") 130 may be positioned so as to view the cuttings that are returned to the surface with the drilling fluid and the captured images may be used to analyze the mineralogy of the subterranean formation. As would be appreciated by those of ordinary skill in the art, with the benefit of this disclosure, the HICM 130 may be placed at any suitable location in the system, such as, for example, at a point along the mud return line 118, the shale shaker 120, and/or the path 132 between the shale shaker 120 and the cuttings disposal area 124, also referred to herein as the disposal path. In one exemplary embodiment, the HICM 130 may be positioned so as to monitor the cuttings on the path 132 between the shale shaker 120 and the cuttings disposal area 124 as this path 132 is typically stationary. Because the path 132 is typically stationary, the use of HICM 130 along this path permits a clearer imaging of the cuttings 134 and of the background. Accordingly, the HICM 130 may be used to continuously monitor the cuttings as they are moved through the system. The ability to continuously monitor to the mineralogy of the subterranean formation of interest is particularly important as often slight changes in mineralogy can be indicative of changes in the bedding plane. Such changes in mineralogy are often not detected when using the prior art batch sampling methods. As would be appreciated by those of ordinary skill in the art, with the benefit of this disclosure, such continuous monitoring of the cuttings has a higher sampling rate than the prior art manual sampling methods discussed above and allows a virtually "real-time" analysis of the formation as the formation is drilled.

The operator may control the operation of the HICM 130 to capture an image that is best suited for the intended analysis. For instance, the operator may zoom in the HICM 130 to obtain an image with a high resolution or may zoom out to capture a lower resolution image of a wider area with a larger number of cuttings 134. The focusing techniques required to change the resolution of the images and/or the area captured in each image are well known to those of ordinary skill in the art and will not be discussed in detail herein. Additionally, the operator may modify the sampling rate of the HICM 130. As would be appreciated by those of ordinary skill in the art, with the benefit of this disclosure, the sampling rate of the HICM should be high enough so that blurring due to motion does not significantly degrade any captured images (i.e. motion should not obscure the identity of the cuttings). Specifically, the continuous monitoring provided by the methods and systems disclosed herein refer to the ability to capture hyperspectral images of the cuttings at a rate that is in a range of between, for example, one image per approximately 1 second and $1/128$th of a second. In one embodiment, the sampling rate may be $1/100$th of a second. Image capture occurs within a time window and is repeated at a certain rate. The time window should be short enough to avoid blurring. The sample rate can be as high as the inverse of the time window. For instance, the time window may be as high as 1 second and short as $1/128^{th}$ of a second while the sample rate may be as low as one sample per second or as high as 128 samples/second. However, the sampling rate of the HICM 130 may be limited by the processing capabilities of the system. In one embodiment, the distance and optics of the HICM 130 may be chosen such that 0.5 [mm] can be easily resolved in the captured images.

In one exemplary embodiment, a cleaner, such as, for example, an orbital mud cleaner, such as that available from Vortex Fluid Systems, Inc., of Tulsa, Okla., may be used to clean the cuttings 134 before they are analyzed by the HICM 130. In one embodiment, the cuttings 134 may be washed before being analyzed by the HICM 130.

In another exemplary embodiment, the cuttings 134 may be analyzed without cleaning. As discussed above with reference to FIG. 1, the fluid portion of the returned mixture which consists of the drilling fluid seeps through the shale shaker 120 screens and into mud pits 122 and the cuttings 134 remain on the shale shaker 120 screens. In one exemplary embodiment, the cuttings 134 may be imaged through the mud background without cleaning. As discussed in more detail below, the portion of the returned fluid that seeps through the shale shaker 120 screen may be used as a control sample to perform differential work on the images of the uncleaned cuttings captured by the HICM 130 to distinguish the portion of the captured image that corresponds to the cuttings 134 from the background mud.

In one exemplary embodiment, the HICM 130 may be selected and positioned such that typical individual cuttings 134 are clearly visible in the captured images. Accordingly, the size of the cuttings 134 to be analyzed may be determined by the user. For instance, in one exemplary embodiment, the cuttings' sizes of interest may vary from 1 [mm] on a side to 1 [cm] on a side.

In one embodiment, the HICM 130 may be used to identify any organic residue present on the cuttings 134. The information about the nature of the organic residue on the cuttings 134 may then be used to identify the particular zone in the subterranean formation where the cuttings 134 originated. In one embodiment, this information may be correlated to a mineral log of the subterranean formation to isolate a particular zone of interest. For instance, the drilling operations may first go through a first zone (e.g. a shale region) with minimal or no hydrocarbon materials. The drilling operations may then proceed to cross into reservoir rock and eventually pass through the reservoir rock and enter another layer with minimal or no hydrocarbon materials. Accordingly, an analysis of the residue on the cuttings returned to the surface by the drilling fluid from this drilling operation may be used to identify each stage of this drilling operation as the amount of oily residue on the cuttings will initially be minimal, increase to a peak value once the operations enter the reservoir rock and slope off as the operations exit the reservoir rock.

In a water based mud system, any oil residue on the cuttings is indicative of an oil bearing zone in the well bore where the drilling operations are being performed. In contrast, in an oil based mud system, the operator may need to distinguish between the portion of the oil residue on the cuttings that is from the drilling mud and the portion of the oil residue that may be from an oil bearing zone in the well bore. To that end, in one exemplary embodiment, the HICM 130 and the portion of the system where images are to be captured may be contained in an enclosure to isolate the image capturing region from ambient light. The portion of the system that is imaged may then be illuminated with a light of known spectral content, such as, for example, fluorescent light. As would be appreciated by those of ordinary skill in the art, with the benefit of this disclosure, having illuminated the imaged portion with a light of known spectral content, the operator may distinguish between the oil residue that is part of the mud and the oil residue from an oil bearing zone in the well bore. Further, in one exemplary embodiment, the operator may illuminate the imaged region with a light of known spectral content to look for one or more specific minerals. As would be appreciated by those of ordinary skill in the art, with the benefit of this disclosure, Ultraviolet, Infrared or other optical bands may be used. In one exemplary embodiment, the wavelength of the light source used may selected from the range between 0.1 [nm] and 2000 [nm].

In one exemplary embodiment, when using an oil based mud, the cuttings may be cleaned with a mixture of soap and water or other suitable cleaning fluids to minimize and/or eliminate the impact of the drilling mud on the images captured by the HICM 130. The use of such cleaning fluids may also remove any oil residue from an oil bearing zone in the wellbore from the surface of the cuttings. However, the cleaning fluids typically do not seep into the cuttings and therefore, and residues that exist inside the cuttings will remain intact. Accordingly, in one exemplary embodiment, once the cuttings are cleaned, they may be smashed and the HICM 130 may capture an image of the powdered cuttings which may be used to deduce the properties of the formation being drilled.

The images captured by the HICM 130 may be processed for lithology identification and for cuttings shape analysis. Suppose that there are h hyperspectral wavelength ranges designated by the set A. For true hyperspectral imaging, the elements of A should be contiguous, i.e., A should be of the form:

$$A=\{(\lambda_0,\lambda_1),(\lambda_1,\lambda_2),(\lambda_2,\lambda_3)\ldots,(\lambda_{h-1},\lambda_h)\}$$

where the $(\lambda_i, \lambda_j)$ designates a wavelength interval from $\lambda_i$ to $\lambda_j$ where $\lambda_i < \lambda_j$ when $i < j$.

Since the mineralogy identification and cuttings shape analysis need not be tied to hyperspectral imaging, the definition of A will be generalized somewhat to $$A=\{(\lambda_{L1},\lambda_{R1}),(\lambda_{L2},\lambda_{R2}),(\lambda_{L3},\lambda_{R3})\ldots,(\lambda_{Lh},\lambda_{Rh})\}$$

where $$\lambda_{Li} < \lambda_{Ri}.$$

Each image will be referred to as a frame.

The frames will be assumed to be rectangular images having M+1 by N+1 pixels for each of the h hyperspectral components. Since it somewhat simplifies the notation, M and N will be assumed to be even. The indices for a pixel will range from −M/2 to M/2 by −N/2 to N/2.

A total of F consecutively sampled frames will be processed simultaneously as will be described below. Once F frames have been processed, the oldest frame can be discarded and a new frame added to the set for processing, or an additional F frames can be acquired for processing. The old frames can be stored in a memory store for later reference or for retrieval for further processing at a later time.

In one exemplary embodiment, a first step in the processing may be to acquire and stack multiple images so as to improve the signal to noise ratio. FIG. 2 depicts an exemplary process for acquiring and stacking multiple images in accordance with an exemplary embodiment of the present invention. As shown in FIG. 2, at step 202, the HICM 130 may be used to acquire F frames of hyperspectral images with cuttings. Next, at step 204, for each of the F frames a hyperspectral component may be selected for cross-correlation processing. At step 206, for each selected hyperspectral component, successive frames are cross-correlated. Accordingly, as would be appreciated by those of ordinary skill in the art, with the benefit of this disclosure, if the frames are grouped into F frames at a time, then there will be F−1 cross-correlation matrices, $C_{h,f,i,j}$. Next, at step 208, for each hyperspectral component and for f=2, 3, . . . , F, find $I0_{h,f}$ and $J0_{h,f}$, the indices at which the value of $C_{h,f,i,j}$ is a maximum. At step 210, for f=2, 3, . . . , F, the averages of $I0_{h,f}$ and $J0_{h,f}$ are calculated over all selected hyperspectral components as:

$$I0f = \frac{1}{NHC}\sum_{h \in HC} I0h, f$$

$$J0f = \frac{1}{NHC}\sum_{h \in HC} J0h, f$$

where NHC is the number of hyperspectral components. Once the averages of $I0_{h,f}$ and $J0_{h,f}$ are calculated, at step 212, $I0_f$ and $J0_f$ may be used to align and stack frames for all hyperspectral components, producing hyperspectral frames $D_{hs,m,n}$, where hs represents the hyperspectral component hs taken from the set of all hyperspectral images. Additionally, at step 214, background hyperspectral images may be established as $B_h$, where h=1, 2, . . . , H. Using the outputs from steps 212 and 214, the background may then be removed at step 216. With the background image removed at step 216, the hyperspectral image analysis may be performed at step 218 and shape processing and characterization may be performed at step 220. As would be appreciated by those of ordinary skill in the art, with the benefit of this disclosure, although FIG. 2 depicts a number of steps for processing images, many of the steps depicted therein are optional and same or similar results may be achieved by eliminating one or more of the recited steps.

Further, it is desirable, but not necessary to establish a background image of the area where cuttings will pass prior to acquiring images of cuttings or to acquire such an image at a time when cuttings are not present. Because the background is present to some extent in all images and has no relation to the formation properties and cuttings' properties sought, it is advantageous from a signal to noise perspective to remove it from all of the frames. For instance, the portion of the returned fluid that seeps through the shale shaker 120 screen may be used as a control sample to perform differential process on the images of the uncleaned cuttings captured by the HICM 130 to distinguish the portion of the captured image that corresponds to the cuttings 134 from the background mud and equipment. Accordingly, once a clean background image has been identified, F frames of hyperspectral images of the cuttings may be obtained. Hyperspectral image analysis and cuttings' shape analysis is possible with the images from individual frames. However, the signal to noise ratio may be improved by processing multiple frames.

In one exemplary embodiment, before processing the hyperspectral images of the cuttings, a set of hyperspectral components may be selected for correlation processing in order to provide a means for aligning successive frames and stacking or averaging them. It is therefore preferred that the components selected be present at a level significantly above the background noise level. In one embodiment, the selected components may be present at a level of at least 3 [dB] above the background noise level. Accordingly, a total of SC hyperspectral components have been selected. A set of such hyperspectral components may be defined as:

$$HC = (hc_1, hc_2, \ldots, hc_{SC})$$

For each hyperspectral component, successive frames may be cross-correlated. In one exemplary embodiment cross-correlation may only be performed on a selected subimage of each frame and not on the entire image. As would be appreciated by those of ordinary skill in the art, with the benefit of this disclosure, performing the cross-correlation only on a selected subimage of each frame may have several advantages. First, it may simplify the calculation of the two-dimensional cross-correlation function (to be defined below). Moreover, doing so may reduce the computation time and result in a larger portion of each image being available for hyperspectral and shape processing. The cross-correlation process requires some overlap of images. As would be appreciated by those of ordinary skill in the art, with the benefit of this disclosure, if small sections are cross-correlated across large sections, a larger portion of the image can be covered by the cross-correlation than if large sections are cross-correlated with large sections.

As would be appreciated by those of ordinary skill in the art, with the benefit of this disclosure, there are many ways of defining a two-dimensional cross-correlation function. In one exemplary embodiment, two even integers may be selected. The image intensities in frame f in a specific hyperspectral interval h may be designated as $I_{h,f,i,j}$, where:

$$h \in HC$$
$$-\frac{M}{2} \leq i \leq \frac{M}{2}$$
$$-\frac{N}{2} \leq j \leq \frac{N}{2}$$

Then the cross-correlation between frames f−1 and f for hyperspectral components h is defined as $$C_{h,f,i,j} = \sum_{jj=-Q/2}^{Q/2} \sum_{ii=-P/2}^{P/2} (I_{h,f-1,ii,jj} - \overline{I_{h,f-1}}) \cdot (I_{h,f,i+ii,j+jj} - \overline{I_{h,f}})$$

where:

$$\frac{P}{2} - \frac{M}{2} \leq i \leq \frac{M}{2} - \frac{P}{2}$$
$$\frac{Q}{2} - \frac{N}{2} \leq j \leq \frac{N}{2} - \frac{Q}{2}$$

and the averages over hyperspectral component h in frames f−1 and f, respectively, may be obtained as:

$$\overline{I_{h,f-1}} = \frac{1}{(M+1) \cdot (N+1)} \sum_{j=-N/2}^{N/2-1} \sum_{i=-M/2}^{M/2-1} I_{h,f-1,i,j}$$

$$\overline{I_{h,f}} = \frac{1}{(M+1) \cdot (N+1)} \sum_{j=-N/2}^{N/2-1} \sum_{i=-M/2}^{M/2-1} I_{h,f,i,j}$$

Generally, the hyperspectral images in frame f are displaced versions of the hyperspectral images in frame f−1, the displacement being common to all hyperspectral components. This displacement is due to motion of the cuttings 134 along the path 132 from the shale shaker 120 to the cuttings disposal area 124, or along the shale shaker 120, if the images are taken of the cuttings on the shale shaker. Because of the choice of indices, if the particles are not moving, $C_{h,f,i,j}$ achieves a maximum at i=0 and j=0. If frame f has been displaced from frame f−1 by $I0_{h,f}$ pixels in the i index and $J0_{h,f}$ pixels in the j index, then the correlation peak will be at element:

$$C_{h,f,-I0_{h,f},-J0_{h,f}}$$

and the two images can be aligned by offsetting the indices in image f by $-I0_{h,f}$ and $-J0_{h,f}$. In one exemplary embodiment, the images may be realigned so that they can be stacked by adding the intensities in realigned images. Because the image boundaries are finite, it may not be possible to combine all elements of both images after shifting.

If more than one hyperspectral component h is used for the correlation analysis, then the average shift indices may be calculated as:

$$I0_f = \frac{1}{NHC} \sum_{h \in HC} I0_{h,f}$$

$$J0_f = \frac{1}{NHC} \sum_{h \in HC} J0_{h,f}$$

where NHC is the number of elements in HC. Next, the images of all of the hyperspectral components of frame f may be aligned with those of f−1 and the two may be added or averaged. This process may be repeated with appropriate shifting to align and stack all F images if desired. The stacked images may be designated as $D_{hs,i,j}$ where hs indicates an element from the set of all hyperspectral wavelengths, A. For each hs, the following relationship is applicable to the i and j components of $D_{hs,i,j}$:

$$\frac{P}{2} - \frac{M}{2} \leq i \leq \frac{M}{2} - \frac{P}{2}$$
$$\frac{Q}{2} - \frac{N}{2} \leq j \leq \frac{N}{2} - \frac{Q}{2}$$

In one exemplary embodiment, an additional step may be carried out in order to remove the background over the same range of indices. As would be appreciated by those of ordinary skill in the art, with the benefit of this disclosure, background removal may not be a matter of simply subtracting all of the pixel values in the background images from all of the values in an image of interest. In fact, background removal is more a matter of knowing which pixel values to subtract. Exemplary methods of performing the background removal are well known to those of ordinary skill in the art and will not be discussed in detail herein. One such method is set forth in, for example, OBJECT TRACKING: A SURVEY, Alper Yilmaz, Omar Javed and Mubarak Shah, ACM Computing Surveys, Vol. 38, No. 4, Article 13, December 2006 (hereinafter "Yilmaz").

Accordingly, $D_{hs,i,j}$ may refer to an image in a spectral band hs whether or not it has been subjected to background removal. The typical hyperspectral imaging techniques may be applied to the full set of $D_{hs,i,j}$ for mineral identification across the image.

Analysis of images may be confined to a particular set of hyperspectral frames of interest because of the correlation between these frames and minerals of interest, or the whole set of hyperspectral frames, or a linear combination of hyperspectral frames, the linear combination selected because of the relative importance of the selected hyperspectral components for identification of a particular mineral of interest.

Figure 3A:
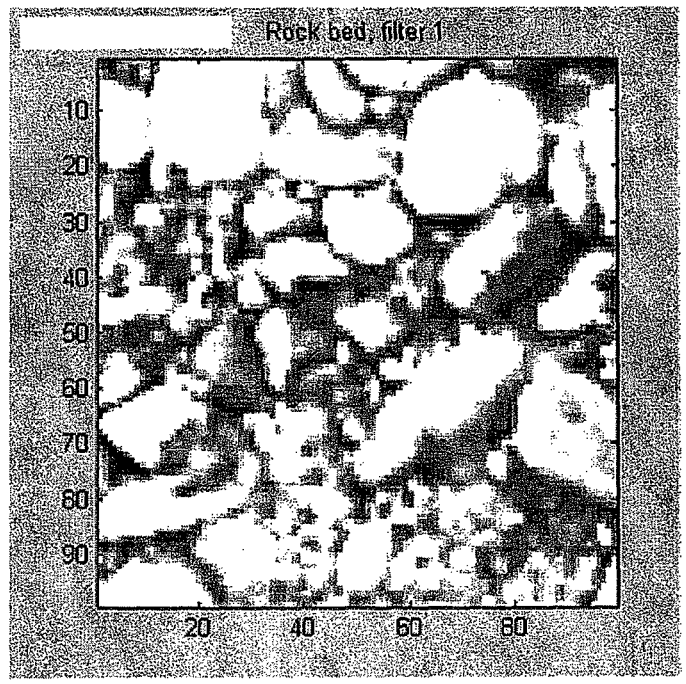
FIGS. 3a, 3b, and 3c. depict an image of a pebble bed captured using different spectral filters.
Figure 4:
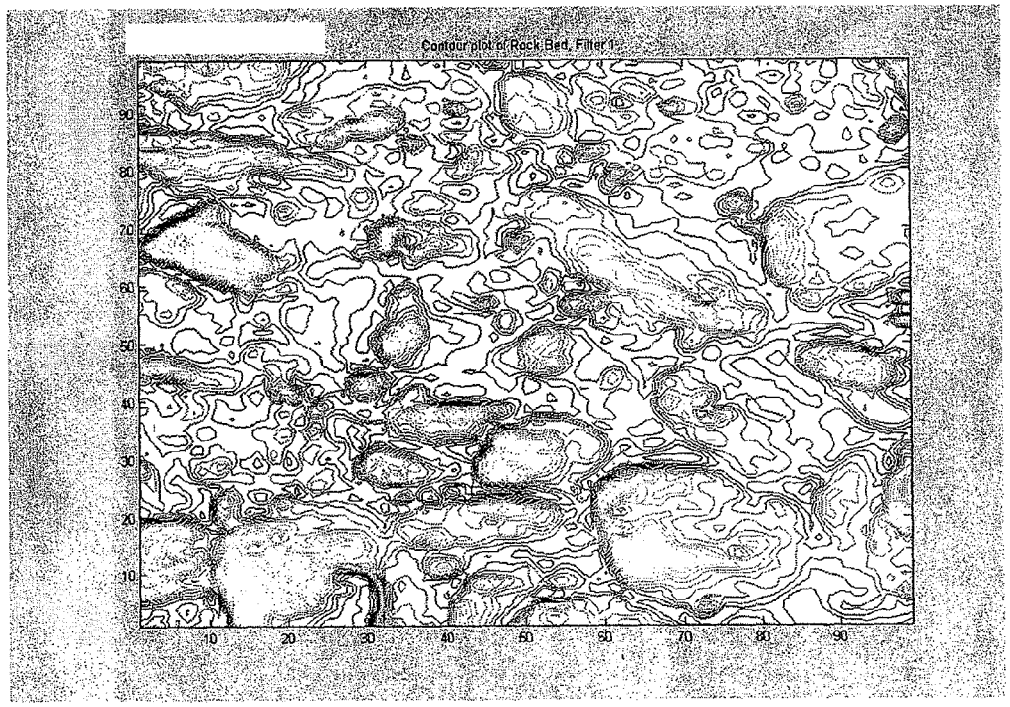
Figure 5:
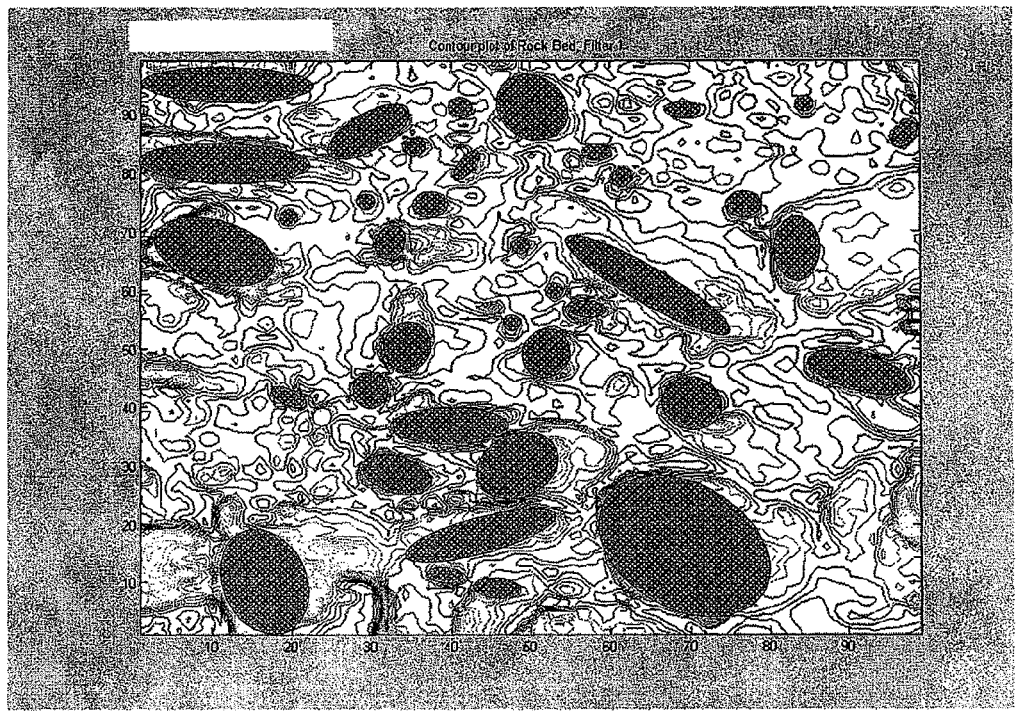
FIG. 5 shows how the contours of FIG. 4 may be approximated by ellipses.

There are several ways of analyzing the shapes of the cuttings. Yilmaz provides a summary of some of these techniques. Some of these techniques such as contouring may be computer intensive while in other techniques, all shapes of interest may be approximated by a simple geometric shape, such as an ellipse. Parameters such as major axis, minor axis, and orientation are estimated for the ellipses, and statistical distributions of the parameters may be compiled to gain an understanding of the size and shape distribution of elements in each image. In another exemplary embodiment, the contours may be used to define closed regions which may then be approximated by geometric shapes. FIGS. 3a. and 4-6 depict images that may be produced using known methods such as those disclosed in Yilmaz. Specifically, FIG. 3a. is an image of a rock bed taken through a spectral filter. Contours of that image are shown in FIG. 4. As would be appreciated by those of ordinary skill in the art, with the benefit of this disclosure, the contours of FIG. 4 may produced in a number of ways, such as, for example, using the Matlab™ software available from MathWorks of Natick, Mass. FIG. 5 shows how the contours may be approximated by ellipses using methods such as those disclosed in Yilmaz. Once the image is broken into such geometrical shapes, the mean dimensions of the shapes may be characterized and subjected to a variety of statistical measures.

Additionally, textural analysis may be applied separately to regions covered by each of the geometric shapes. In one exemplary embodiment, the texture analysis techniques may be a fractal analysis or a two-dimensional Fourier analysis.

An example of a fractal analysis is disclosed by Roland Kraft and Josef Kaner in "ESTIMATING THE FRACTAL DIMENSION FROM DIGITIZED IMAGES", and is available at http://tka4.org/materials/lib/Articles-Books/DSP/Fractals/ALG.PDF. Additional information regarding the fractal analysis is available in, for example, "FRACTAL-BASED DESCRIPTION OF NATURAL SCENES," IEEE Transactions on Pattern Analysis and Machine Intelligence, PAMI-6. pp. 661-674, 1984.

Figure 6:
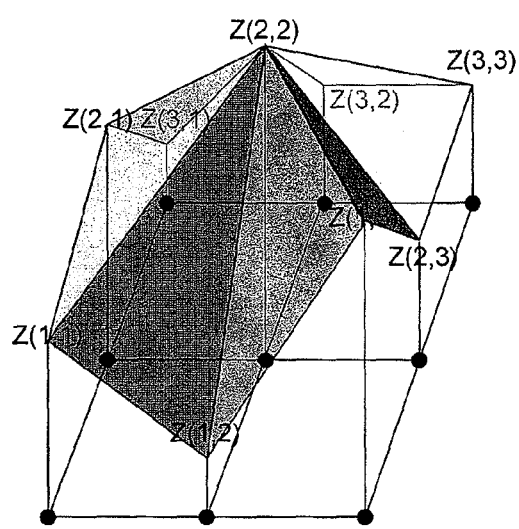
FIG. 6 shows a triangulation scheme used in fractal image analysis.

FIG. 6 depicts a 3 pixel by 3 pixel subimage extracted from an image. The image intensities are represented in this figure as heights above a plane. A triangulation may be carried out across the surface defined by these heights with the triangles joined at the elevation of the center pixel. Fractal analysis may be carried out by breaking the entire image into 3×3 subsets of the form shown in FIG. 6 over a number of different length scales and calculating the total area of the triangles as a function of the length scale. As would be appreciated by those of ordinary skill in the art, with the benefit of this disclosure, alternatively, fractal analysis may be carried out on a subset of an image.

At the finest scale in the fractal analysis, the triangulation may be carried out over successive pixels, so the basic length may be the unit of length of the side of a pixel which may be assumed to be a square to simply the analysis. At coarser scales, a larger length may be chosen, such as, for example, the width of two pixels. The intensity values at the selected pixels may be selected directly from the image, or because of the increased scale, may be average values based on neighboring pixels. As would be appreciated by those of ordinary skill in the art, with the benefit of this disclosure, the scale values used need not be an integer number of pixels as it is possible to interpolate values between measured image intensities.

Figure 7:
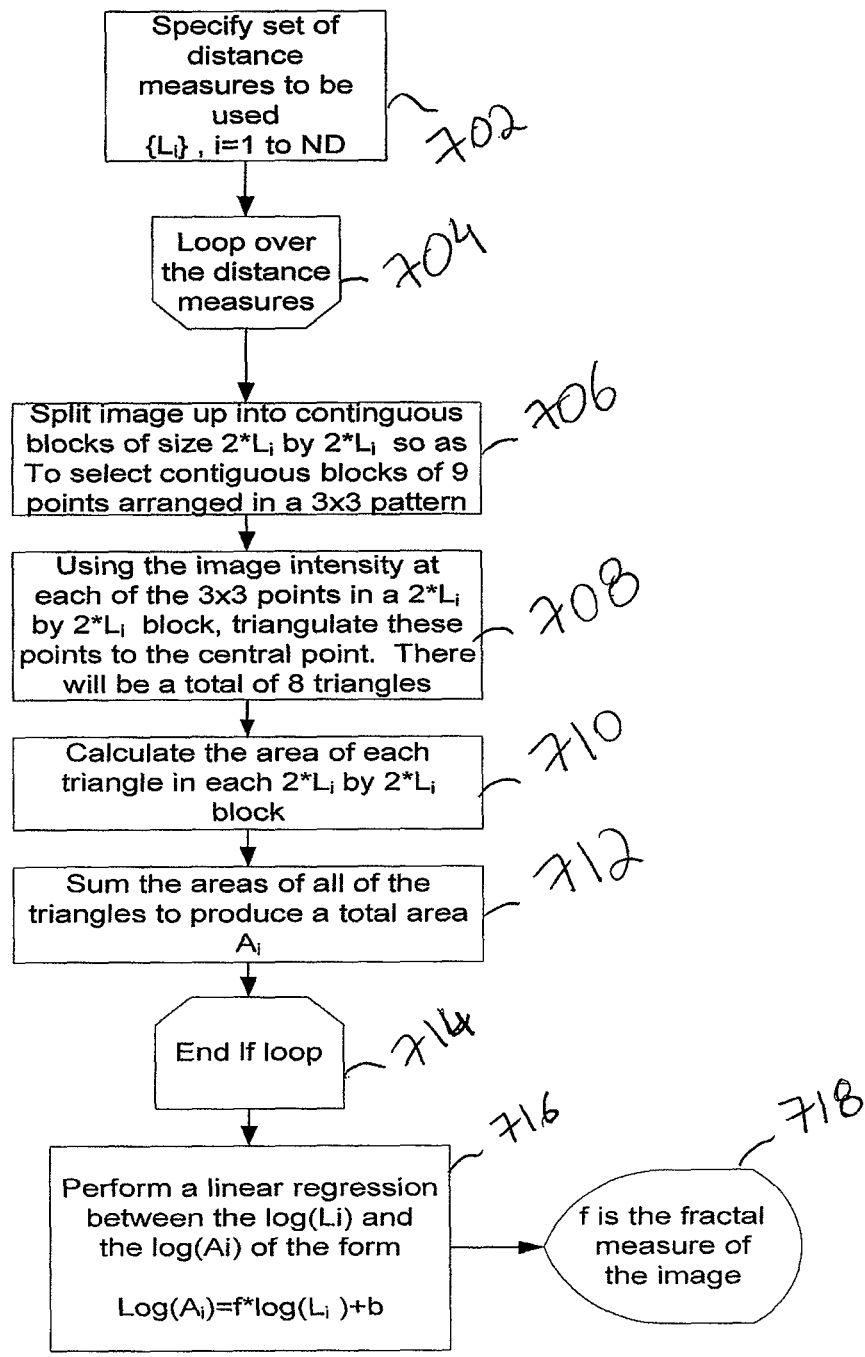
FIG. 7 shows a general procedure for fractal analysis of an image in accordance with an exemplary embodiment of the present invention.

FIG. 7 depicts general exemplary method steps for carrying out a fractal analysis in accordance with an embodiment of the present invention. As shown in FIG. 7, at step 702, the basic length to be used is designated as $L_i$. If the values of $L_i$ are multiples of the basic spacing between pixels, it may not be possible to tile the entire image at each scale. This may result in extra variability in area calculation which can be compensated by normalizing over the total area that serves as the base of the triangles (i.e. the Cartesian plane of the image), with minimal impact on the fractal index that is calculated. When using $L_i$ values that are a significant fraction of the overall Cartesian dimensions of the image (i.e. large $L_i$ values), the calculated areas may vary significantly and erratically. Accordingly, in one embodiment, the basic length to be used, $L_i$, may be selected so that it is not larger than approximately 10% of the shortest side of an image. With this restriction on the range of values of $L_i$, a useful fractal-type parameter f may be calculated for an image frame (or subset thereof) by making a linear fit to the logarithm calculated areas $A_i$ to the logarithm of the lengths $L_i$ of the form:

$$\text{Log}(A_i) = f \cdot \text{Log}(L_i) + b$$

where b is a constant.

Figure 3B:
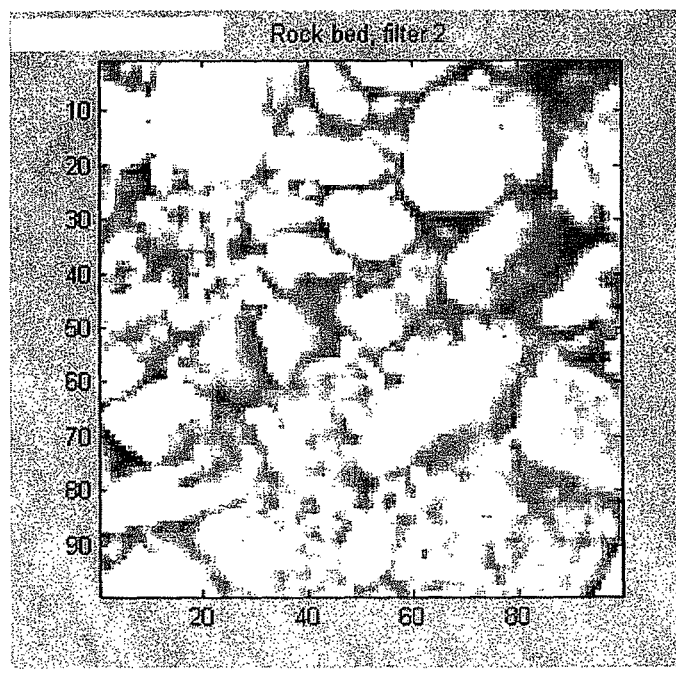
Figure 3C:
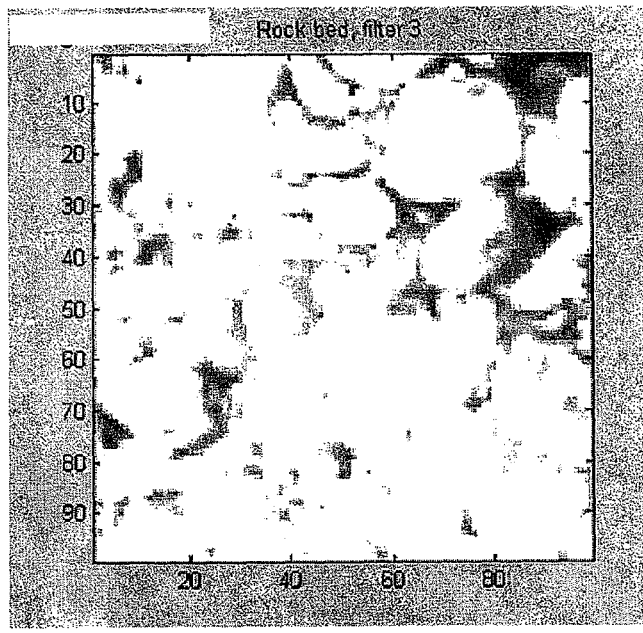
Figure 8:
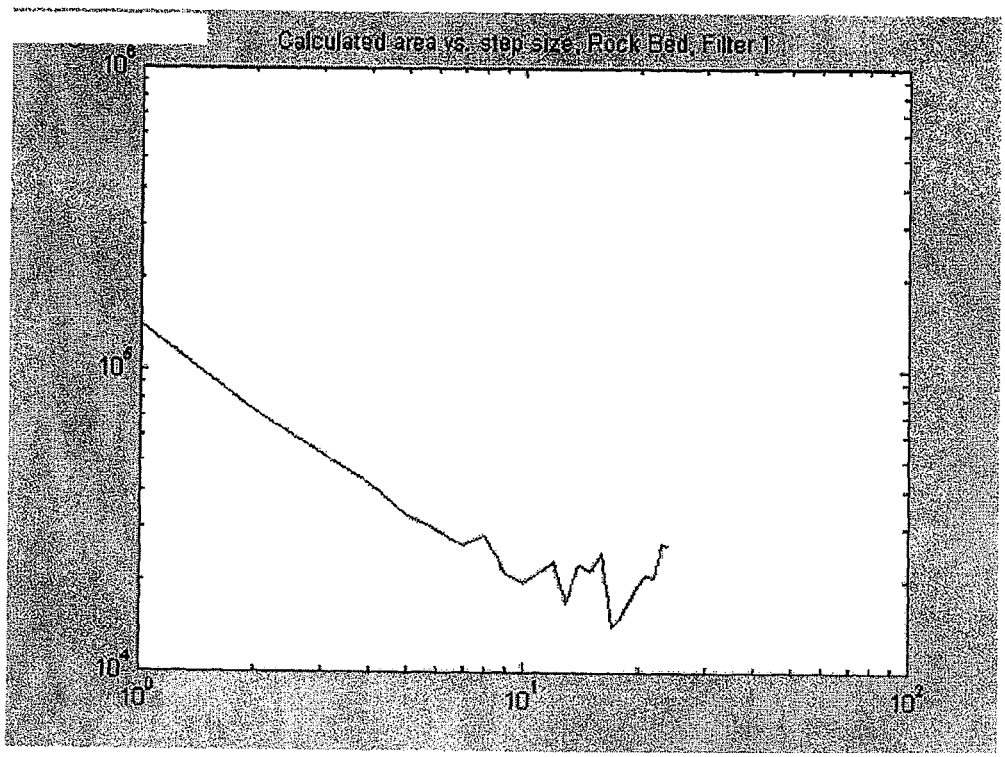

FIGS. 3a-3c depict an image of a group of pebbles taken through three different wavelength filters, filter 1, filter 2, and filter 3, respectively, using a HICM. These images may be subjected to a fractal analysis in accordance with an exemplary embodiment of the present invention. In one exemplary embodiment, each image may contain 99×99 pixels. FIG. 8 depicts how the calculated area varies with step size for the image of FIG. 3a. As shown in FIG. 8, the smaller the step size, the larger the area. Further, as shown in FIG. 8 and discussed above, there is a limiting step size point at which the area starts to become erratic. This increase in area with decreasing scale length is to be expected as smaller scales include progressively more "bumps" and "dimples" in the image.

Figure 9A:
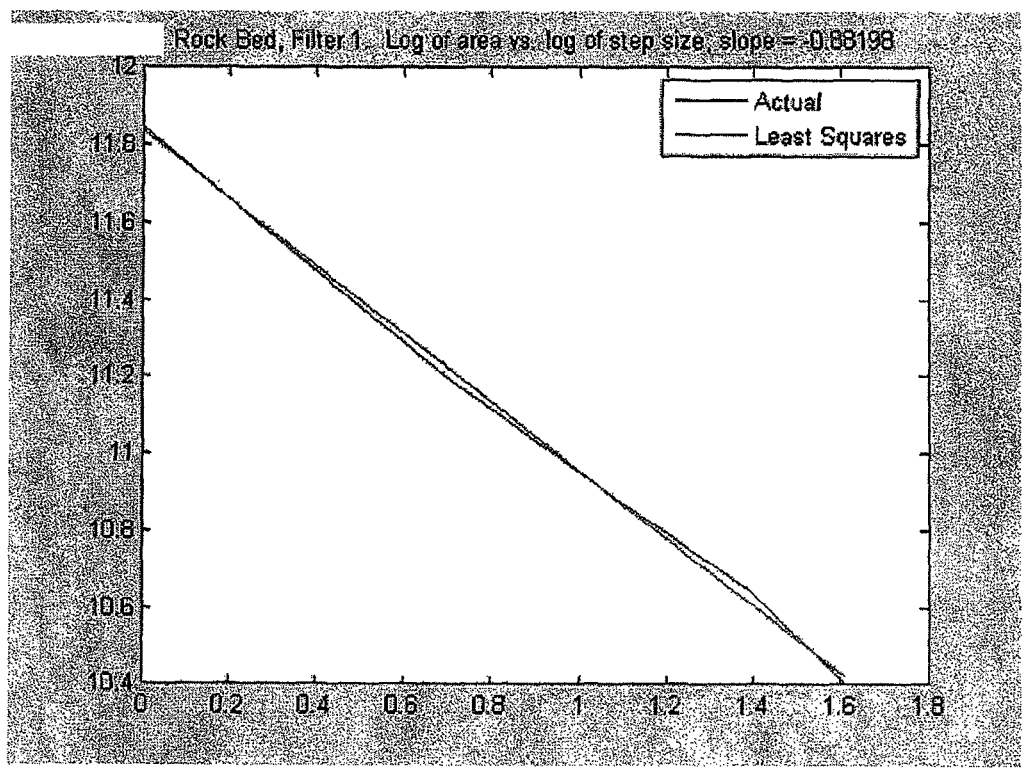
FIGS. 9a, 9b, and 9c. show the least squares fit to the areas obtained with the fractal analysis of the images in FIGS. 3a, 3b, and 3c, respectively.
Figure 9B:
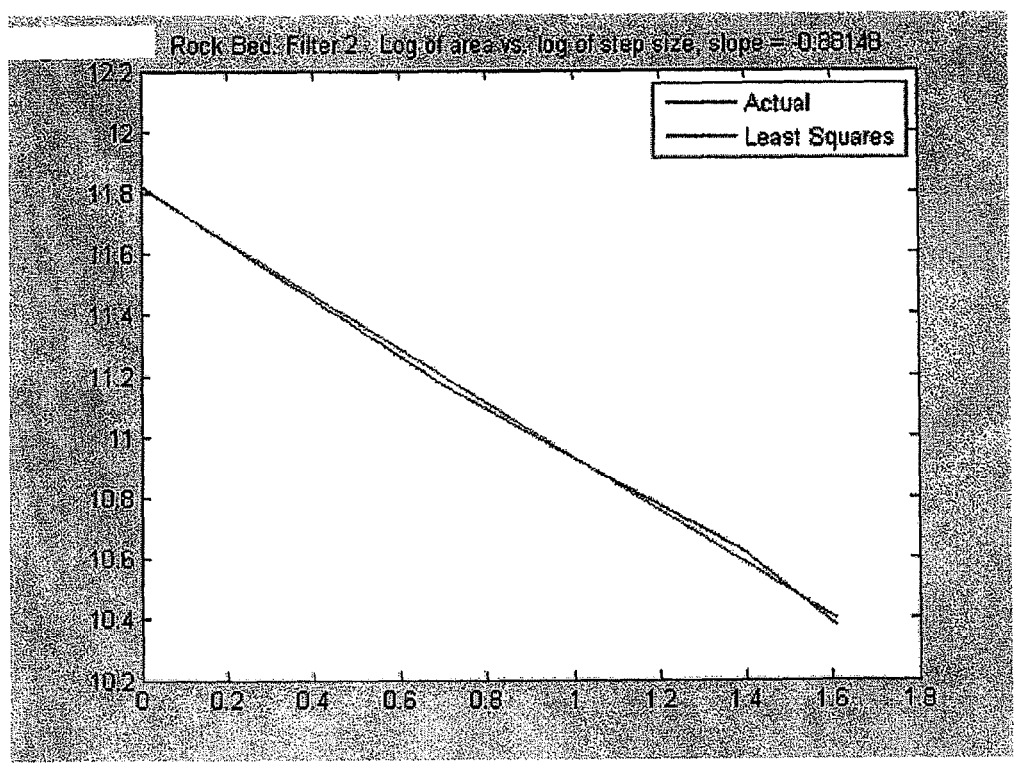
Figure 9C:
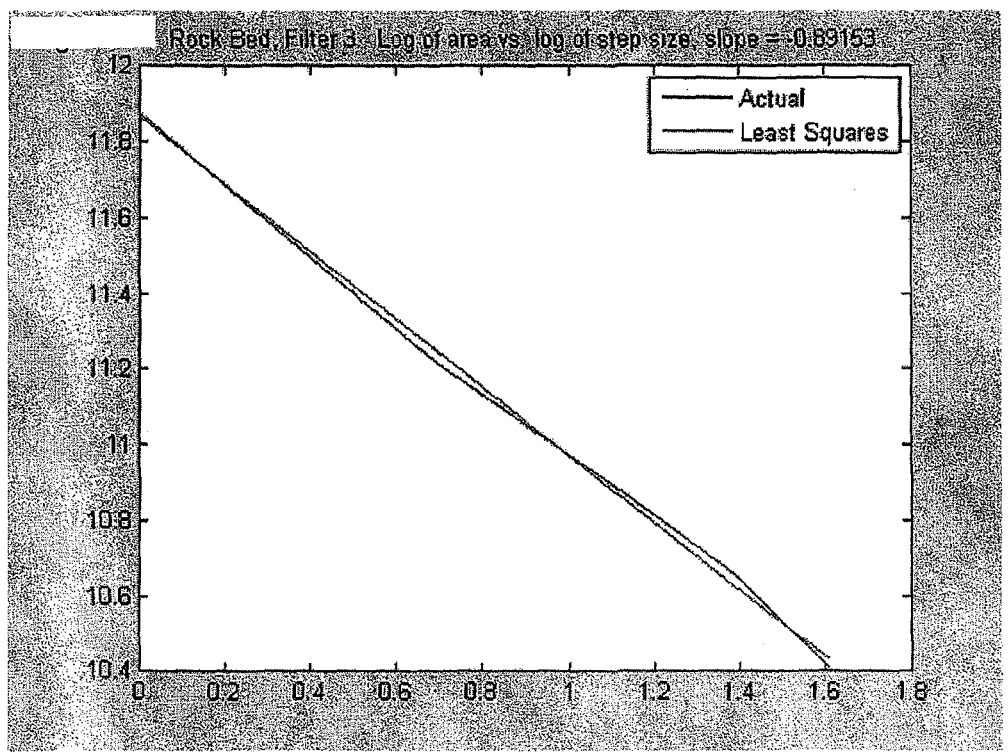
Figure 10:
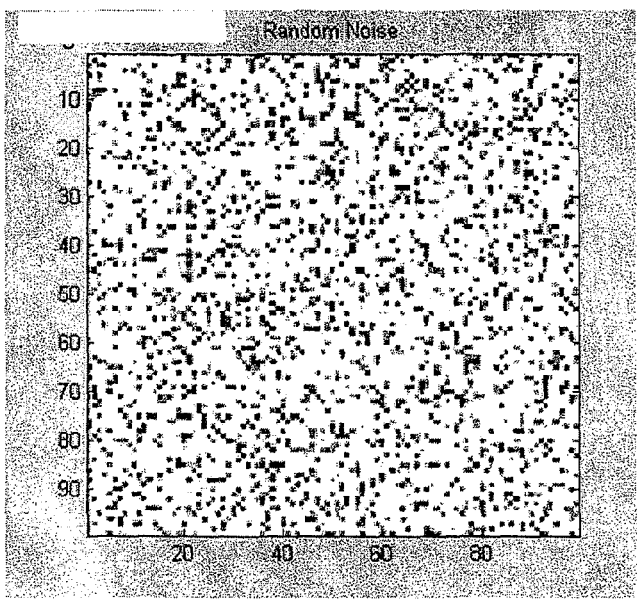
FIG. 10 shows an image obtained by generating a random grid of 99×99 intensities with a standard uniform distribution between 0 and 1 and scaling the results by 255.
Figure 11:
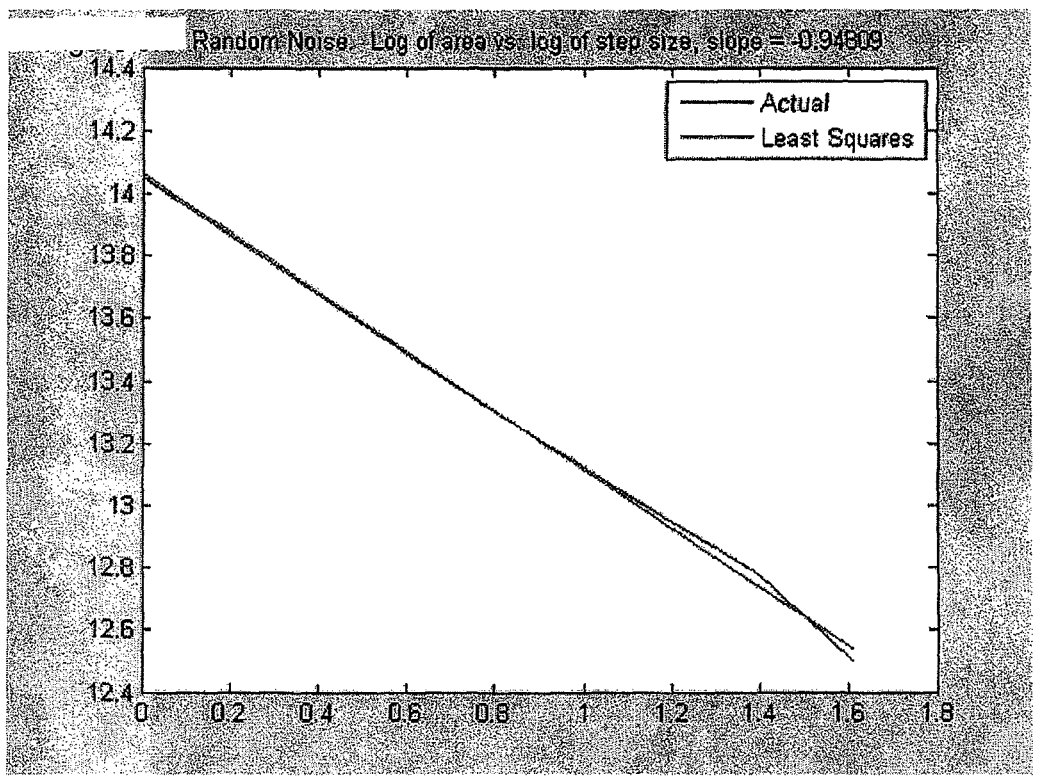
FIG. 11 shows the fractal analysis of the image on FIG. 10.

FIGS. 9a, 9b, and 9c show the least squares fit to the areas obtained with the fractal analysis of the images in FIGS. 3a, 3b, and 3c, respectively. As shown in FIG. 9, a small fractal index was obtained in each case. FIG. 10 was obtained by generating a random grid of 99×99 intensities with a standard uniform distribution between 0 and 1 and scaling the results by 255. FIG. 11 shows the fractal analysis of the image in FIG. 10. Because of the higher level of randomness, the magnitude of the fractal index is larger than in FIG. 9.

Figure 12:
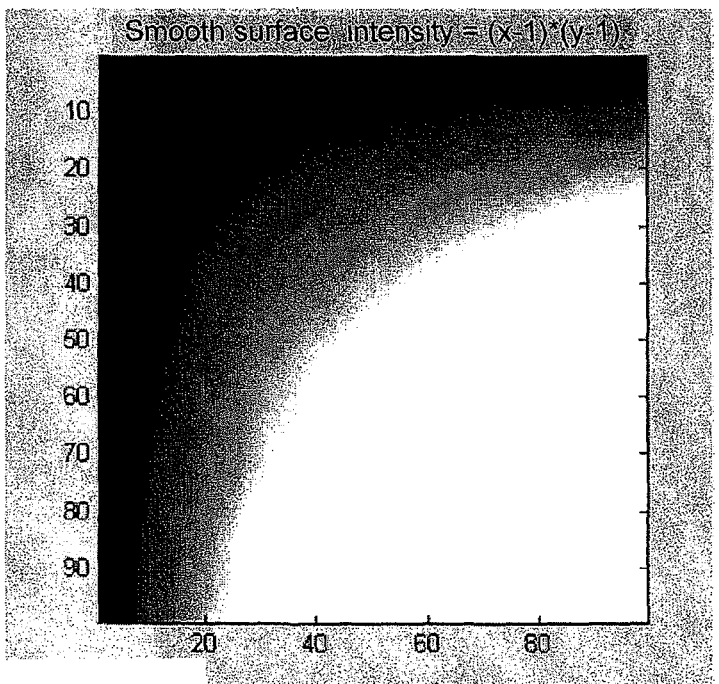
FIG. 12 depicts an image produced with intensities calculated as $(x-1)*(y-1)$ where x is the horizontal pixel index and y is the vertical pixel index.
Figure 13:
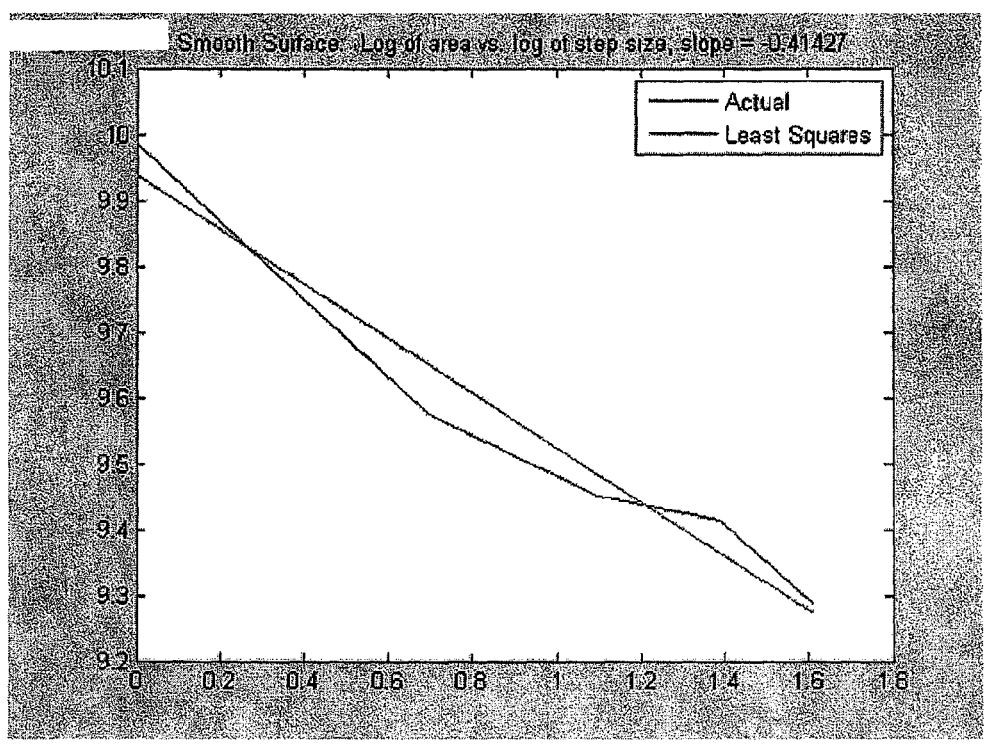
FIG. 13 shows a fractal analysis of the image of FIG. 12.

Accordingly, the less variation there is in an image, the smaller is the magnitude of the fractal dimension. This is illustrated in FIGS. 12 and 13. The image in FIG. 12 was produced with intensities calculated as $(x-1)*(y-1)$ where x is the horizontal pixel index and y is the vertical pixel index. The fractal analysis is shown in FIG. 13. The magnitude of the fractal index is considerably less than in the previous examples. If the image is completely featureless, the value of f obtained is always close to 0. Accordingly, the fractal index may provide a useful measure of the variability of the intensity of an image, which is related to the distribution of the cutting sizes as in FIGS. 3, 8, and 9.

Figure 14:
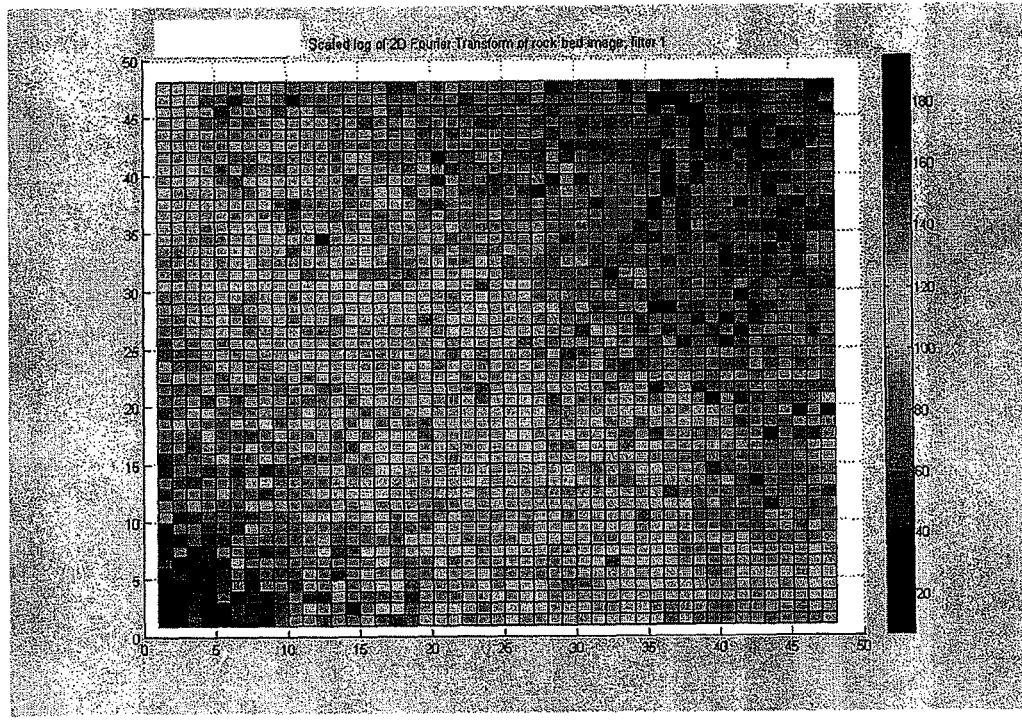
Figure 15:
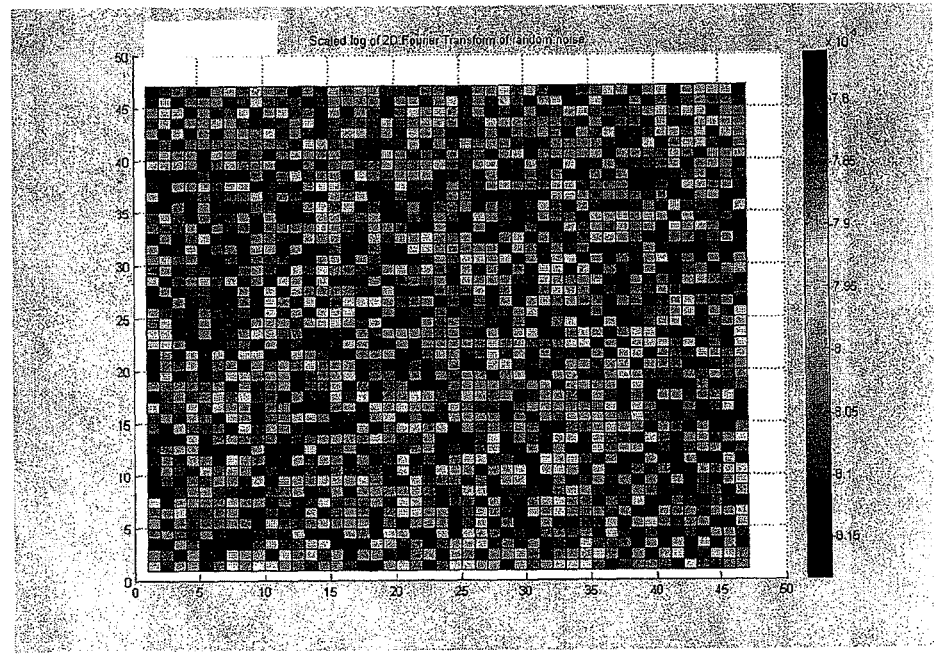
FIG. 15 shows a two-dimensional Fourier transform of the image of FIG. 8.
Figure 16:
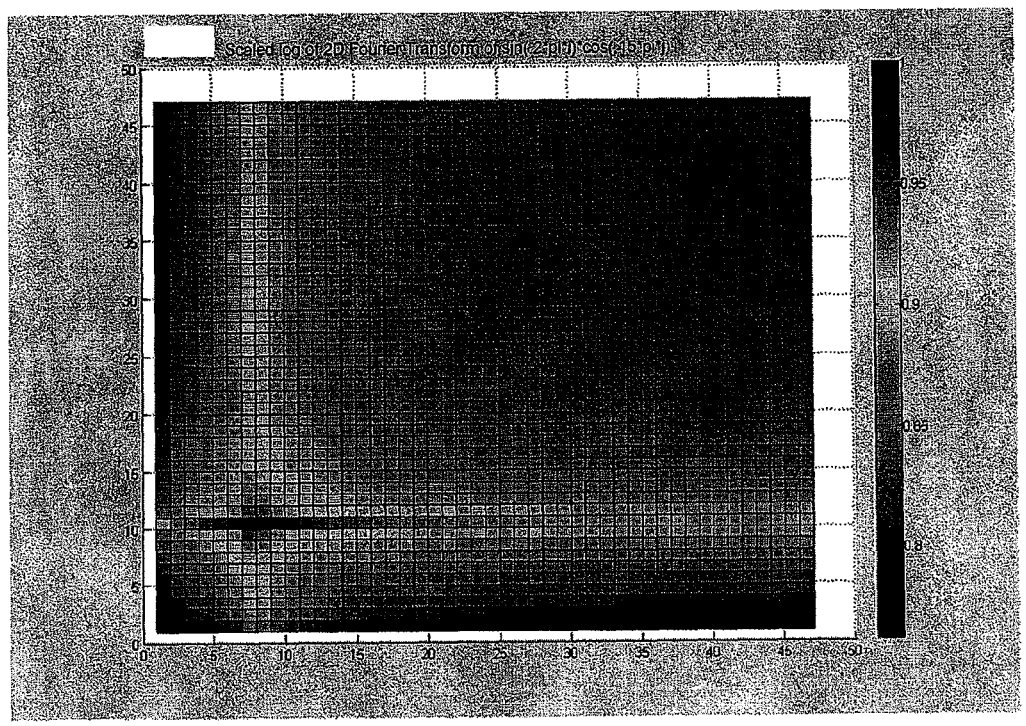
FIG. 16 shows an image derived from a two-dimensional periodic function, with a single periodicity along the horizontal axis and a single periodicity along the vertical axis.

In one exemplary embodiment, a two dimensional Fourier transform may be used to analyze the images captured by the HICM 130. In one embodiment, the intensity values of each image may be interpreted as a matrix of numbers similar to the cross-correlation analysis discussed above. The intensity values along a column in the matrix may be treated as one-dimensional signals and their Fourier transforms may be taken. This results in another matrix. The rows of this new matrix may be treated as signals and their Fourier transforms may be taken. Finally, the log of the modulus of the Fourier transform may be calculated at each position in the matrix. These may then be displayed as images, with the color of an image pixel varying according to the log of the modulus of the two-dimensional Fourier transform at that pixel. FIGS. 14, 15, and 16 depict two-dimensional Fourier transforms of images of FIGS. 3a, 8, and a periodic image to be described in more detail below, respectively. The ordinate and abscissa of each image is proportional to the wave number. Stated otherwise, the ordinate and abscissa of each image is inversely proportional to the physical wavelength of image features. The images may be cropped such that the DC (infinite wavelength) values are eliminated and the shortest wavelength is twice the spatial sampling interval.

As shown in FIG. 14, the image is dominated by low wave numbers (or long wavelengths). This is a result of most of the pebbles of FIG. 3a occupying a significant fraction of the image. In contrast, the image in FIG. 15 shows a broad distribution of wave numbers, and hence of wave lengths, as there is no characteristic scale in the corresponding image as shown in FIG. 8. FIG. 16 shows an image derived from a two-dimensional periodic function, with a single periodicity along the horizontal axis and a single periodicity along the vertical axis. In this case, the wave numbers that dominate the image are a result of these periodicities. Accordingly, as with fractal analysis, in one embodiment, a two-dimensional Fourier transform may be used to understand the distribution of sizes in an image captured by the HICM 130.

Figure 17:
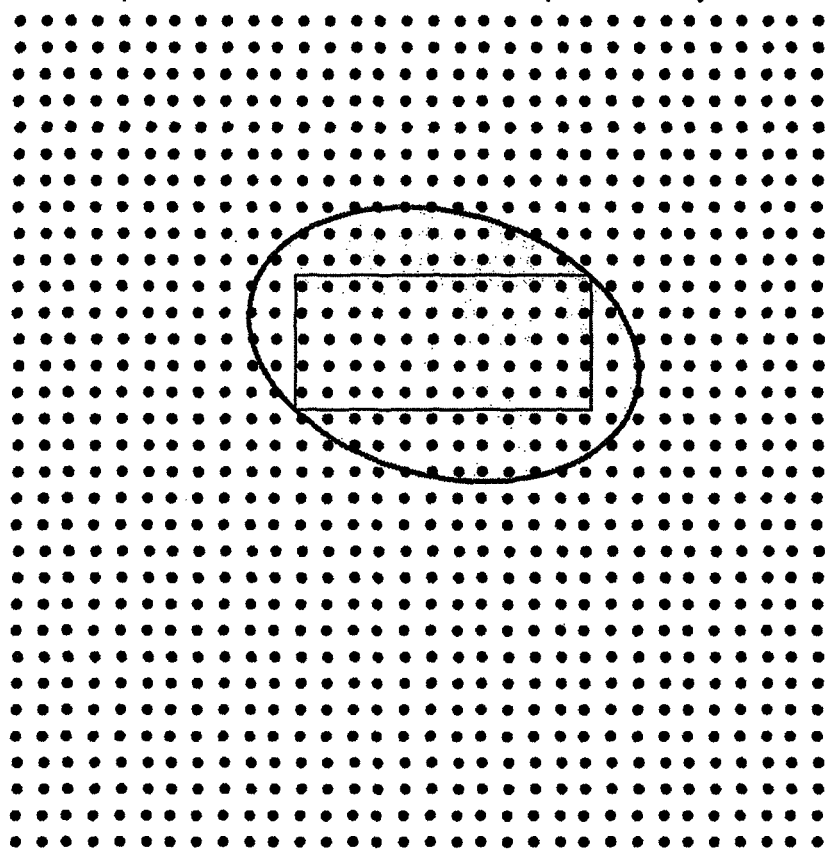
FIG. 17 shows the alignment of a rectangular area within a selected ellipsoid for further textural and/or spectral analysis.

As discussed above, FIG. 5 represents a decomposition of the image of FIG. 3a into a set of ellipses. If the image has a sufficient number of pixels, regions of the image from which the ellipses were derived may be selected within the interiors of the ellipses for further textural analysis. With the techniques disclosed herein, it is best to inscribe a rectangle within each ellipse of the maximum allowable area without exceeding the boundaries of that ellipse and extract the pixels enclosed within that rectangle. Unless the image is to be interpolated in further processing, the rectangle must be aligned with the coordinate system of the image as shown in FIG. 17. In addition to textural processing of this region of the image, either over all hyperspectral wavelengths, or at selected hyperspectral wavelengths, or in linear combinations of images at different hyperspectral wavelengths, the hyperspectra may be analyzed within these regions for mineralogy. Statistics may then be compiled on mineral distribution using all of the regions that have been selected.

Although the present invention is discussed in conjunction with subterranean hydrocarbon operations, as would be appreciated by those of ordinary skill in the art, with the benefit of this disclosure, the methods and systems disclosed herein are not limited to such applications. For instance, the methods and systems disclosed herein may also be used in other industries and applications, such as, for example, copper mining and other mining operations where it is desirable to monitor lithology and/or mineralogy of a formation.

Accordingly, hyperspectral analysis may be used to analyze the shape and/or size of the cuttings returned to the surface by the drilling mud. That information may be used to determine, for example, where in the wellbore the cuttings came from. Further, because the drilling mud has a known Particle Size Distribution ("PSD"), once the size of the cuttings have been determined from the hyperspectral image, it is easy to distinguish the well bore cuttings from the drilling mud particles as the cuttings fall outside the PSD range of the drilling mud.

In one exemplary embodiment, the hyperspectral imaging of the cuttings may be used to identify the zones that are more fracturable. Specifically, different layers in the subterranean formation are made up of different materials which have differing brittleness. The more brittle the minerals in a zone, the easier it is to fracture the formation in that zone. Once the mineralogy of the cuttings is determined, that information may be used to deduce the brittleness and therefore, the fracturability of the formation zone being drilled.

The present invention is therefore well-adapted to carry out the objects and attain the ends mentioned, as well as those that are inherent therein. While the invention has been depicted, described and is defined by references to examples of the invention, such a reference does not imply a limitation on the invention, and no such limitation is to be inferred. The invention is capable of considerable modification, alteration and equivalents in form and function, as will occur to those ordinarily skilled in the art having the benefit of this disclosure. The depicted and described examples are not exhaustive of the invention. Consequently, the invention is intended to be limited only by the spirit and scope of the appended claims, giving full cognizance to equivalents in all respects.

What is claimed is:

1. A method of analyzing a wellbore during drilling operations comprising:
   retrieving a mixture of cuttings and a fluid from the wellbore;
   directing the mixture of cuttings and the fluid to a screen;
   directing the cuttings through a path to a cutting disposal area;
   capturing a hyperspectral image of the cuttings while the cuttings are on at least one of the screen and the path to the cutting disposal area;
   analyzing a shape of the cuttings using the hyperspectral image;

analyzing the hyperspectral image to identify the presence of hydrocarbon on surfaces of the cuttings; and determining at least one of a mineralogy and a lithology of the wellbore using the analysis of the hyperspectral image of the cuttings.

2. The method of claim 1, wherein analyzing the hyperspectral image of the cuttings further comprises analyzing at least one of texture of the cuttings, size of the cuttings, and identification of residue on the cuttings.

3. The method of claim 2, wherein analyzing the texture of the cuttings comprises performing at least one of a fractal analysis and a two-dimensional Fourier analysis.

4. The method of claim 1, wherein the fluid is a drilling fluid.

5. The method of claim 1, wherein the cuttings are cleaned before capturing a hyperspectral image of the cuttings.

6. The method of claim 1, further comprising:
isolating the cuttings from ambient light,
illuminating the cuttings with a light of known spectral content; and
identifying one or more predetermined materials on the cuttings.

7. The method of claim 1, wherein the captured hyperspectral image of the cuttings while the cuttings are on at least one of the screen and the path to the cutting disposal area, comprises a background hyperspectral image and a cuttings' hyperspectral image, further comprising:
identifying the background hyperspectral image;
removing the background hyperspectral image from the captured hyperspectral image of the cuttings while the cuttings are on at least one of the screen and the path to the cutting disposal area; and
determining the cuttings' hyperspectral image.

8. The method of claim 1, further comprising determining brittleness of a portion of the wellbore using the determined mineralogy of the wellbore and using the determined brittleness to identify a portion of the wellbore to fracture.

9. The method of claim 1, further comprising obtaining a hyperspectral image of the fluid as a control sample and performing differential work using the captured hyperspectral image of the cuttings and the captured hyperspectral image of the control sample, wherein the captured hyperspectral image of the cuttings represents the cuttings in an uncleaned state.

10. A system for monitoring formation characteristics comprising:
a drill bit for drilling the formation;
a mud pump for pumping a drilling fluid to the drill bit;
a mud return line for returning the drilling fluid from the drill bit;
wherein the returned drilling fluid comprises a fluid portion and formation cuttings;
a shale shaker for separating the fluid portion from the formation cuttings;
wherein the shale shaker comprises a disposal path for disposing of the formation cuttings;
a hyperspectral image capture mechanism for capturing a hyperspectral image of the formation cuttings;
wherein the hyperspectral image of the formation cuttings is captured on at least one of the shale shaker and the disposal path;
wherein the captured hyperspectral image of the formation cuttings is used to determine shape of the cuttings;
wherein the captured hyperspectral image of the formation cuttings is used to identify the presence of hydrocarbon on surfaces of the cuttings; and
wherein the captured hyperspectral image of the formation cuttings is analyzed to monitor formation characteristics.

11. The system of claim 10, wherein at least one of image resolution, image capture area, and image sampling rate is set by an operator.

12. The system of claim 10, wherein the formation characteristics comprise at least one of formation mineralogy and formation lithology.

13. A method of characterizing a formation comprising:
drilling a well bore in the formation;
retrieving cuttings from the well bore while drilling the formation;
continuously obtaining a hyperspectral image of the cuttings;
determining shape of the cuttings using the hyperspectral image;
identifying the presence of hydrocarbon on surfaces of the cuttings using the hyperspectral image; and
analyzing the obtained hyperspectral image of the cuttings to determine formation characteristics.

14. The method of claim 13, wherein retrieving cuttings from the well bore comprises:
pumping a drilling fluid into the well bore;
retrieving a mixture of the drilling fluid and cuttings from the well bore; and
separating the cuttings from the well bore from the mixture of the drilling fluid.

15. The method of claim 13, wherein the formation characteristics comprise at least one of formation mineralogy and formation lithology.

16. The method of claim 13, wherein continuously obtaining a hyperspectral image of the cuttings comprises capturing one of 100 images per second and 128 images per second.

17. The method of claim 13, wherein analyzing the obtained hyperspectral image of the cuttings comprises analyzing at least one of shape of the cuttings, texture of the cuttings, size of the cuttings, and identification of residue on the cuttings.

18. The method of claim 17, wherein analyzing the texture of the cuttings comprises performing at least one of a fractal analysis and a two-dimensional Fourier analysis.

19. The method of claim 13, wherein the cuttings are cleaned before obtaining a hyperspectral image of the cuttings.

20. The method of claim 13, further comprising:
isolating the cuttings from ambient light,
illuminating the cuttings with a light of known spectral content; and
identifying one or more predetermined materials on the cuttings.

21. The method of claim 20, wherein the light of known spectral content is selected from the group consisting of ultraviolet, infrared and visible light.

22. The method of claim 13, wherein the obtained hyperspectral image of the cuttings comprises a background hyperspectral image and a cuttings' hyperspectral image, further comprising:
identifying the background hyperspectral image;
removing the background hyperspectral image from the obtained hyperspectral image of the cuttings; and
determining the cuttings' hyperspectral image.

* * * * *